United States Patent [19]

Lee

[11] 4,402,670
[45] Sep. 6, 1983

[54] THREE-DIMENSIONALLY ADJUSTABLE SUPPORTING AND LOCKING MECHANISM

[76] Inventor: Tsung-Li Lee, 245 W. Garvey Ave., Monterey Park, Calif. 91754

[21] Appl. No.: 295,378

[22] Filed: Aug. 24, 1981

[51] Int. Cl.³ .............................................. A61C 11/00
[52] U.S. Cl. ..................................................... 433/61
[58] Field of Search ................. 433/61, 62, 64; 269/75

[56] References Cited

U.S. PATENT DOCUMENTS 2,070,025  2/1937  Phillips ................................... 433/64
2,212,953  8/1940  Popp et al. ............................. 269/75

*Primary Examiner*—Robert Peshock
*Attorney, Agent, or Firm*—Gene W. Arant; Paul H. Ware

[57] ABSTRACT

A mechanism for locking a dental model in a desired position of adjustment includes a sphere, an elongated member extending through an opening in the sphere, and means for gripping the sphere in a selected rotational position while at the same time gripping the elongated member in a selected longitudinal position.

3 Claims, 5 Drawing Figures

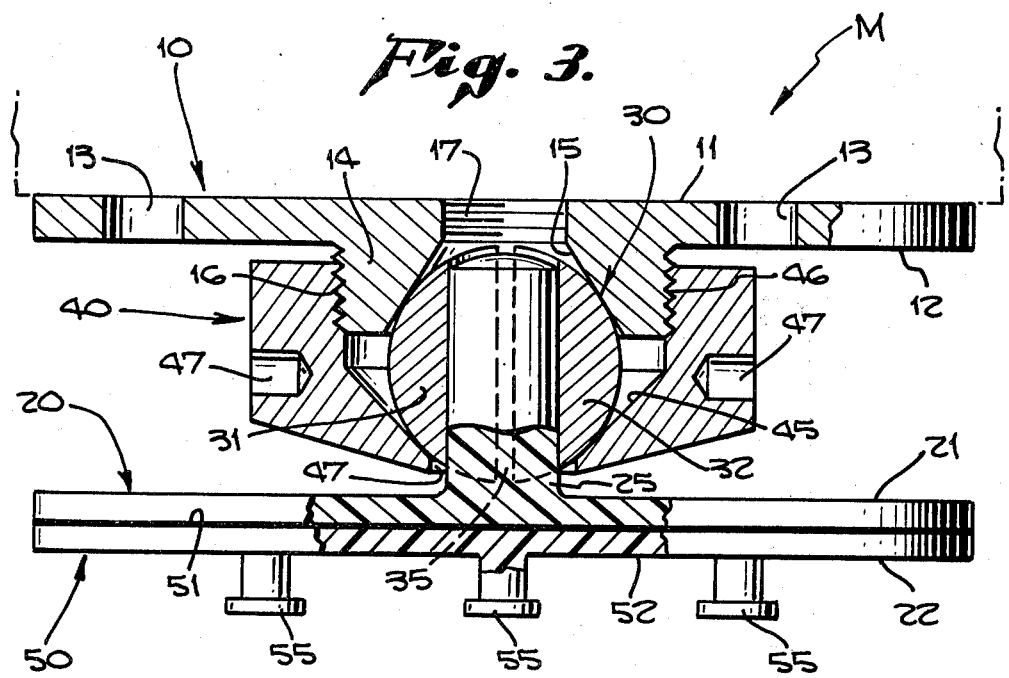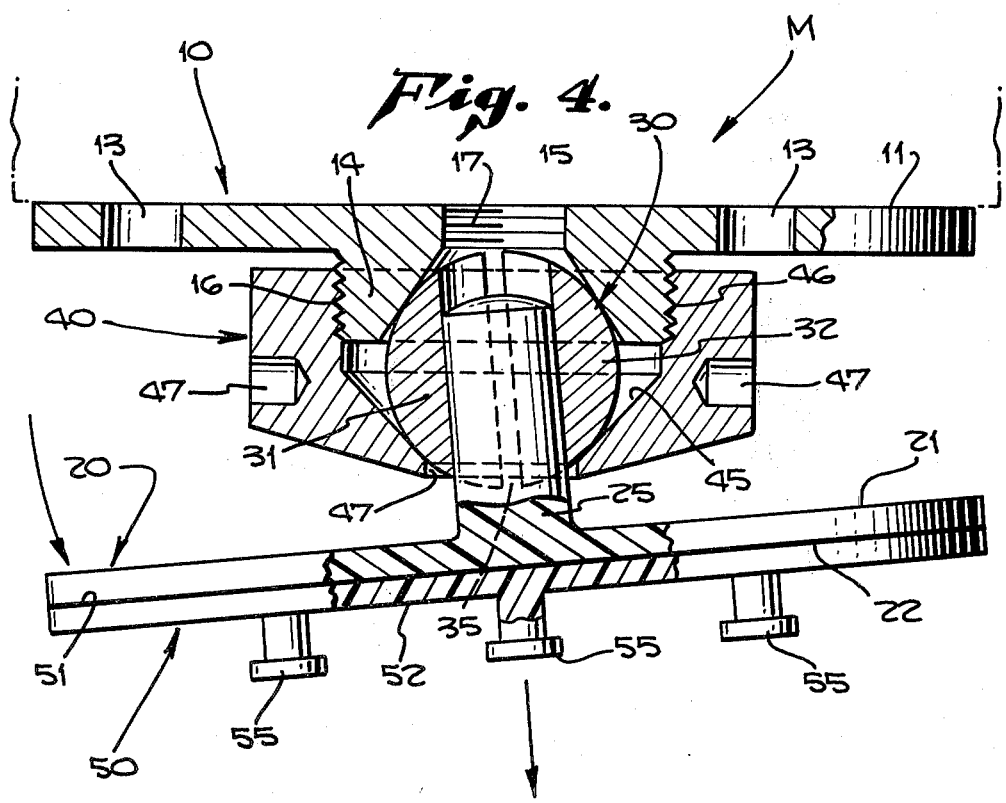

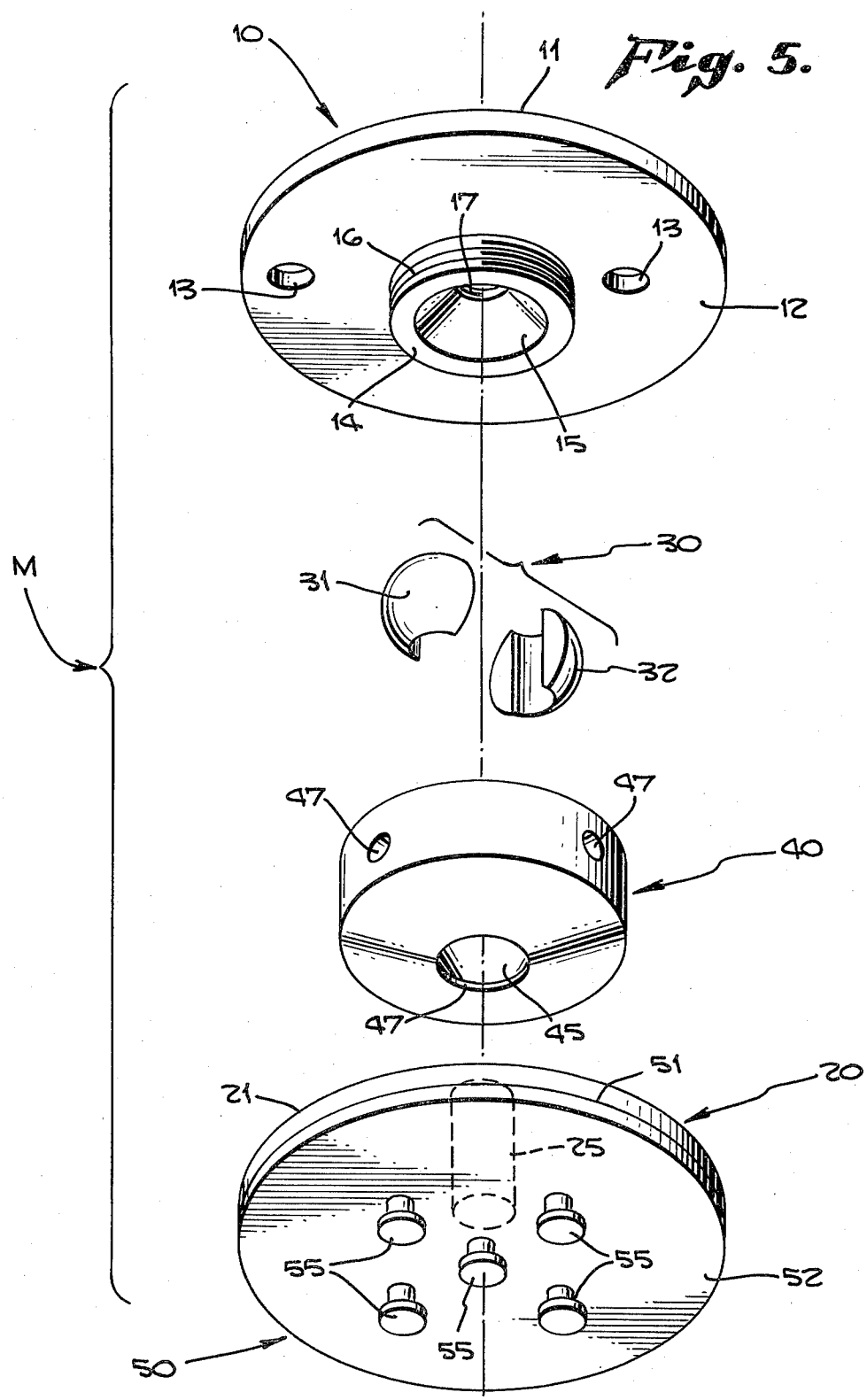

THREE-DIMENSIONALLY ADJUSTABLE SUPPORTING AND LOCKING MECHANISM

BACKGROUND OF THE INVENTION

There are many applications which involve measuring, adjusting, or reproducing the position of a solid body in three dimensions. One of these many applications is in the field of dentistry.

In performing full-mouth rehabilitation it is necessary to repair natural teeth, and/or to construct crowns, bridges, and the like. When the tooth structures have thus been rehabilitated it is necessary that the closing of the mouth will provide a proper static fit of the lower teeth upon the upper teeth. Furthermore, the slopes of the chewing surfaces on the teeth must be properly fashioned so that the dynamic action of the teeth, either in chewing or in bruxing, will be proper.

It is common practice to use the indirect method of dentistry in which full or partial models of the patient's tooth structures are made, and these models are then mounted upon a device known as a dental articulator in order to complete the shaping of the crowns, bridges, or other restorations. The articulator has an upper plate which simulates the upper jaw or maxilla, and it also has a lower plate which simulates the lower jaw or mandible. Each tooth model must be attached to the corresponding plate of the articulator in a precisely determined three-dimensional position, in order to properly simulate the patient's chewing mechanism. It has been the common practice of the profession to secure the tooth model to the articulator plate by filling the gap between these two members with plaster of paris, which then solidifies and becomes "stone." That procedure, however, requires a considerable amount of the doctor's time.

Thus the principal object of the present invention is to provide a mechanism for supporting a solid body, permitting the position of the body to be adjusted in three dimensions as desired, and then securely locking the body in its desired position.

A more specific object of the invention is to provide a mechanism of the foregoing type which is particularly adapted for use in the practice of dentistry, in mounting a dental model to the corresponding plate of a dental articulator.

DRAWING SUMMARY

FIG. 3 is vertical cross-sectional view taken on line 3—3 of FIG. 1;

FIG. 4 is a view like FIG. 3, but showing the mechanism in a different position of adjustment; and FIG. 5 is an exploded perspective view of the mechanism of the present invention showing its component parts.

PREFERRED EMBODIMENT

Figure 1:
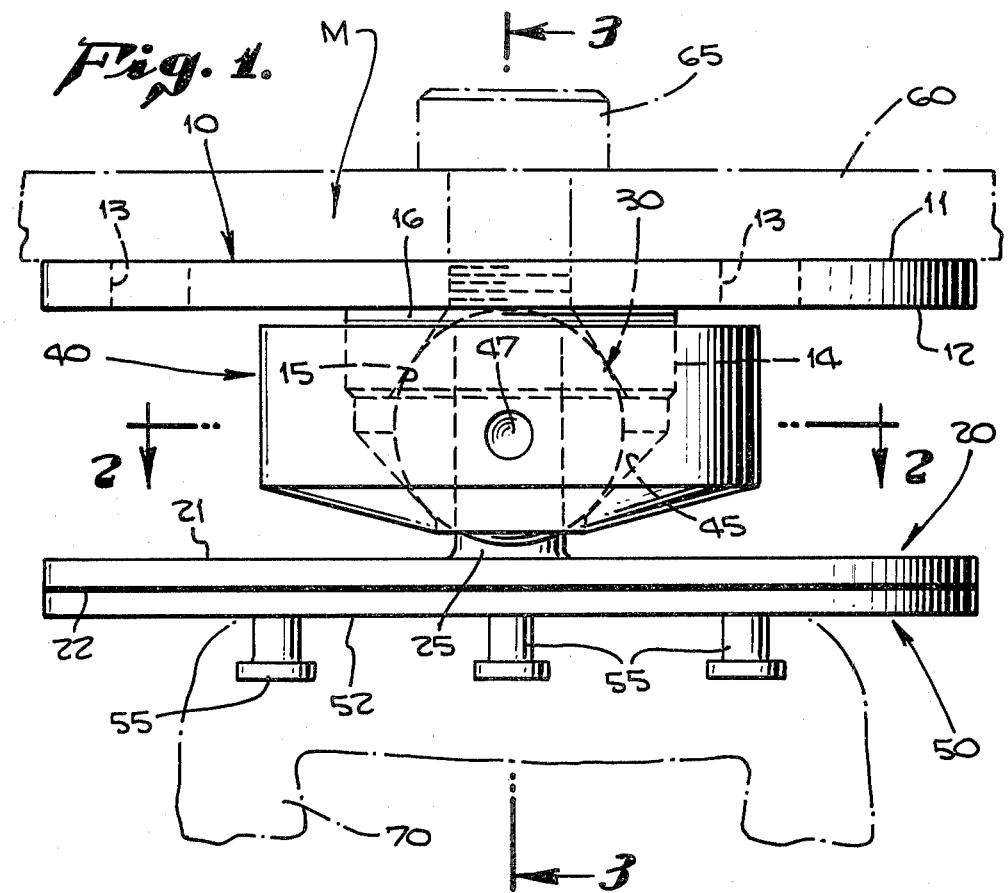
FIG. 1 is an elevation view of the present invention in its assembled condition, and also showing in dotted lines an articulator upper plate, and a dental model which is supported by the adjustable mechanism of the present invention.

Referring now to the drawings, the adjustable mechanism M is perhaps most easily understood with reference to FIG. 5 showing all of its component parts in an exploded relationship. These parts include a first or upper support member 10, a second or lower support member 20, a gripping ring 30, and a locking ring 40.

There is also a third support member 50, shown at the bottom of FIG. 5, which is used in dentistry for purposes of attachment of a dental model. In other applications of my adjustable support mechanism, however, the third support member 50 may not be required.

In the presently preferred embodiment of the invention, the first or upper support member 10 has a generally flat circular configuration, with an upper flat surface 11 and a lower flat surface 12. A pair of smooth-bored holes 13 are provided in the member 10 for aligning it upon a pair of dowel pins, not specifically shown, that are provided on the associated surface of the articulator plate. First support member 10 also has a central hub 14 depending downward from its underside, and an upwardly tapering conical opening or recess 15 is provided inside this hub. The exterior cylindrical surface of the hub 14 is threaded at 16. Threaded surface 16 is substantially concentric to the recess 15, and preferably is precisely concentric thereto. At the upper end of recess 15 a threaded opening 17 communicates with the upper surface 11 of the support member 10. See FIG. 3.

The second or lower support member 20 is preferably also in the form of a flat circular plate. It has a flat upper surface 21 and a flat lower surface 22. A cylindrical post 25 which is integrally formed as part of the support member 20 projects upwardly from its center. The diameter of post 25 is such that it is substantially less than the diameter of recess 15 at its outer or lower end, and in fact, is somewhat smaller than the diameter of recess 15 at its upper end where it merges into the threaded opening 17. The importance of this relationship will be apparent from later description.

Figure 2:
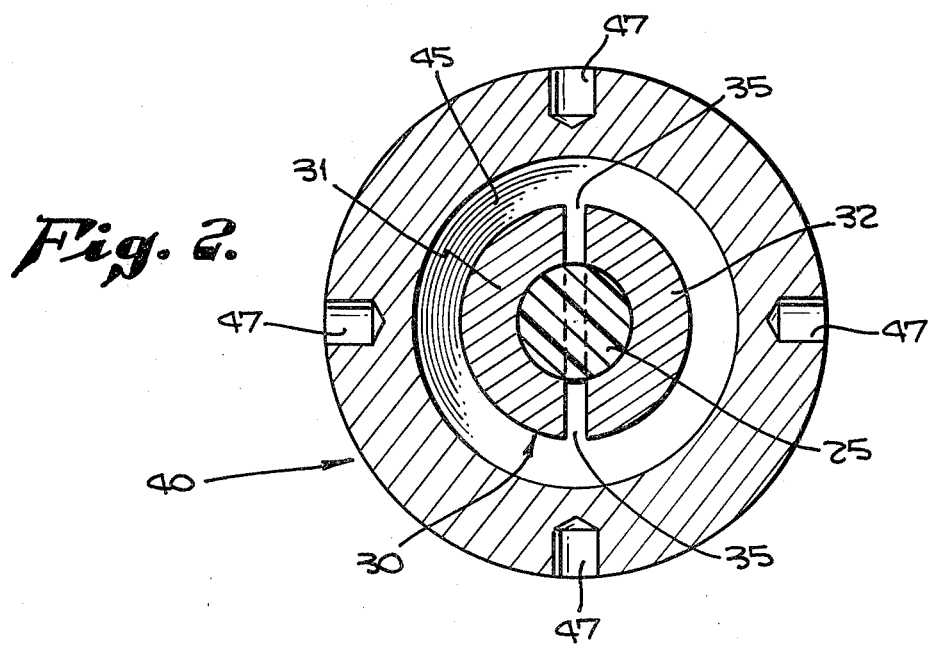
FIG. 2 is a transverse cross-sectional view of the adjustable mechanism taken on line 2—2 of FIG. 1.

The gripping ring 30 is made from sphere segments 31, 32, although in general it may be made from any larger number of sphere segments if that were desired. The segments fit upon the post 25 in such a way as to provide at least one radial gap 35, as best seen in FIG. 2. Although FIG. 2 illustrates that two such gaps are present in the particular illustrated form of the mechanism, it is in general necessary to have only one such gap.

The size, shape, and function of gripping ring 30 will perhaps be better understood from the following brief description of how it can be manufactured. A perfect sphere may be selected, which is of such size that some portion, but less than half, of it can fit into the recess 15 of upper support member 10. The next step is to drill a hole through the sphere, the hole being of exactly the same diameter as post 25. With the hole cut out, the post could then be inserted inside the sphere. The next step in construction would be to cut the sphere with a saw, at two or more points around its circumference, in a radial direction relative to the longitudinal axis of the previously cut central hole. This cutting action will produce two or more segments, depending upon how many cuts are made. The cutting action will also remove sufficient material to ensure that there is at least one radial gap in the gripping ring assembly. It should be understood that some different method for manufacturing the sphere segments 31, 32 may be preferred, but the foregoing description does serve to explain the shapes of the parts.

Locking ring 40 has an essentially cup-shaped configuration. In its lower interior portion it has a conically shaped wall 45 which tapers to its smallest diameter near the bottom of the cup. Its upper interior wall is of cylindrical configuration and is threaded at 46. See FIGS. 3 and 4. The diameter of the threaded wall 46 is the same as the diameter of conical interior wall 45 at its upper or larger end. Locking ring 40 also has an opening 47 in its bottom wall which is located at the lower or smaller end of the conical wall 45. Circumferentially spaced in its exterior cylindrical surface the locking ring 40 has four gripping recesses 47. The purpose of the recesses 47 is to permit convenient gripping of the locking ring with a wrench or the like, for purpose of imparting a turning movement to it.

OPERATION, IN GENERAL

The general operation of my novel supporting and locking mechanism is as follows. It is possible to support the second or lower support member 20 at a desired distance below the first or upper support member 10. It is also possible to twist the second or lower support member 20 in any desired direction so that its angular position relative to the first or upper support member 10 may be whatever is desired. The mechanism can then be locked so as to fixedly secure the two support members in their desired positions relative to each other.

This action is accomplished as follows. The post 25 of lower support member 20 is inserted through the bottom opening 47 of the locking ring 40. Then the various spherical segments which make up the gripping ring 30 are dropped into the open upper end of the locking ring, so that they will occupy positions about the post 25. Locking ring 40 is then moved underneath the upper or first support member 10, and the interior threads 46 of the locking ring are engaged upon the exterior thread 16 of hub 14 of the upper support member. The locking ring is then tightened sufficiently to force the spherical segments of the gripping ring to assume appropriate positions relative to each other, but not so tightly as to produce a locking action.

The next step is to move the post 25 longitudinally inside the gripping ring, so as to establish a desired amount of separation between the two support members 10 and 20. Then the two support members may be twisted relative to each other, and this action is permitted by virtue of the rotation of the gripping ring within the chamber that is cooperatively provided by recess 15 and conical interior wall 45. When a desired relative position of the two support members is achieved, the locking ring 40 is then rotated further so as to lock the interior parts in their positions.

More specifically, recess 15 and conical interior wall 45 cooperate for squeezing the spherical segments of gripping ring 30 together. Due to the radial gap 35, the gripping ring is able to effectively reduce its inner diameter, thus achieving a tight gripping action on the post 25. Recess 15 and conical wall 45, by tightly gripping the ring 30, also prevent its further rotation.

APPLICATION TO DENTISTRY

The present invention is used in dentistry in the following manner. The third support member 50 is in the form of a flat circular plate whose upper surface 51 is adapted to be adhesively secured to the flat lower surface 22 of the second support member 20. From the bottom surface 52 of the third support member 50 there are a plurality of lugs 55 which project downwardly, each lug having an enlarged lower end. A dental model such as that shown by dotted lines 70 in FIG. 1 is cast on the bottom surface 52 of the support member 50, and is therefore securely retained by the lugs 55.

Upper support member 10 is placed underneath an articulator upper plate 60, shown in dotted lines in FIG. 1. As previously stated, the holes 13 then fit over corresponding dowel pins, not specifically shown. A thumbscrew 65, shown in FIG. 1 in dotted lines, is inserted through an opening in the articulator upper plate 60 and thence into the threaded opening 17 in upper support member 10, for securing the upper support member to the articulator plate.

After support member 10 is secured to plate 60, the lower support member 20, locking ring 40, and gripping ring 30 are assembled together in the manner previously described. Locking ring 40 is then secured to the threaded surface 16 of upper support member 10. A special measuring instrument is then used to establish the desired position of the dental model 70 relative to the articulator upper plate 60.

The special dental instrument is known as a transfer face bow. It is first used to measure the position of the patient's upper tooth structure relative to his cranium or maxilla. Then it is used in conjunction with the articulator to establish the same position of the dental model 70 relative to articulator upper plate 60.

Since locking ring 40 remains relatively loose on the threaded surface 16, the second support member 20 will rest upon the upper surface of third support member 50. This establishes both the desired separation of support member 20 from support member 10, and also its desired angular position. Then the locking ring is further tightened, thereby securing support member 10 in its desired position relative to support member 10.

It should also be pointed out that for use in dentistry, certain parts of mechanism M are made of metal and are permanent, while other parts are made of plastic and are disposable. Specifically, the upper support member 10, the gripping ring 30, and the locking ring 40 are made of metal. The lower support member 20 is made of plastic, and the third support member, or model attachment plate, 50, is also made of plastic.

Thus with the dental model 70 in its desired position, and the mechanism M adjusted and locked, the next step is to permanently secure the plates 20 and 50 together. This is done by temporarily lifting the articulator plate 60 and with it all of the upper parts of mechanism M. The flat upper surface 51 of support member 50 is then painted with chloroform. Articulator plate 60 is then returned to its original position so that the surfaces 22, 51 are in mutual engagement. The parts are held in that position for a sufficient period of time for a chemical action to take place, with the result that the two disposable plastic members 20, 50 are securely fastened together.

In the practice of dentistry it is convenient to remove the dental model 70 from the articulator, removing with it of course the plates 20 and 50 which are secured to each other and to the model. Then another patient case can be mounted on the articulator instrument. But at a later time the second case can be removed and the first case can again be placed in the instrument, by again using the transfer face bow in the same manner as previously.

The invention has been described in considerable detail in order to comply with the patent laws by providing a full public disclosure of at least one of its forms. However, such detailed description is not intended in any way to limit the broad features or principles of the invention, or the scope of patent monopoly to be granted.

What is claimed is:

1. An adjustable support mechanism comprising, in combination:
   a first support member having a conically shaped, inwardly tapering recess and having a threaded cylindrical exterior surface which is substantially concentric to said recess;
   a second support member having a projecting cylindrical post whose diameter is substantially smaller than the outer end of said recess;
   a gripping ring adapted to fit about said post, said gripping ring consisting of a plurality of radially arranged sphere segments, said gripping ring having at least one radial gap therein between adjacent segments; and
   a locking ring adapted to fit about said gripping ring, having an interiorly threaded end adapted to engage the threaded outer surface of said first support member, and also having a conical interior wall adapted to cooperate with said conical recess for squeezing respective sides of said gripping ring;
   whereby said post may be slid longitudinally within said gripping ring to position said second support member a desired distance from said first support member, said second member may be twisted as desired relative to said first support member resulting in a corresponding rotation of said gripping ring within said conical wall and conical recess, and then said locking member may be tightened upon said first support member;
   thereby locking said two support members in their desired position of adjustment.

2. An adjustable support mechanism specifically adapted for use in dentistry, comprising the mechanism as claimed in claim 1, and further including a third support member adapted for attachment of a dental model thereto, said third support member being also adapted to be securely attached in a fixed position to said second support member.

3. An adjustable support mechanism specifically adapted for use in dentistry, comprising in combination:
   a first metal support member having a conically shaped, inwardly tapering recess and having a threaded cylindrical exterior surface which is substantially concentric to said recess;
   a second support member made of plastic having a projecting cylindrical post whose diameter is substantially smaller than the outer end of said recess;
   a metal gripping ring adapted to fit about said post, said gripping ring consisting of a plurality of radially arranged sphere segments, said gripping ring having at least one radial gap therein between adjacent segments;
   a metal locking ring adapted to fit about said metal gripping ring, having an interiorly threaded end adapted to engage the threaded outer surface of said first metal support member, and also having a conical interior wall adapted to cooperate with said conical recess for squeezing respective sides of said metal gripping ring; and
   a third support member made of plastic and adapted for attachment of a dental model thereto, said third support member being also adapted to be securely attached in a fixed relative position to said second support member;
   whereby said post may be slid longitudinally within said gripping ring to position said second support member a desired distance from said first support member, said second member may be twisted as desired relative to said first support member resulting in a corresponding rotation of said gripping ring within said conical wall and conical recess, and then said locking member may be tightened upon said first support member;
   thereby locking said first and second support members and thus also said third support member in their desired positions of adjustment.

* * * * *